United States Patent [19]

Meyer

[11] Patent Number: 5,282,744
[45] Date of Patent: Feb. 1, 1994

[54] DENTAL VACUUM PUMP SYSTEM

[76] Inventor: Robert A. Meyer, P.O. Box 279, Spearfish, S. Dak. 57783

[21] Appl. No.: 949,354

[22] Filed: Sep. 23, 1992

Related U.S. Application Data

[63] Continuation of Ser. No. 178,864, Apr. 4, 1988, abandoned, which is a continuation of Ser. No. 477,519, Mar. 21, 1983, abandoned.

[51] Int. Cl.$^5$ ............................................. A61C 17/06
[52] U.S. Cl. ....................................... 433/92; 604/319
[58] Field of Search ................... 433/92; 55/358, 383, 55/385 R, 429, 437, 439; 417/362, 363; 604/35, 319, 320; 419/83

[56] References Cited

U.S. PATENT DOCUMENTS

| | | | |
|---|---|---|---|
| 1,349,766 | 8/1920 | Hunt | 433/92 |
| 2,136,098 | 11/1938 | Browne | 417/362 |
| 2,264,616 | 12/1941 | Buckbee | 418/83 |
| 2,812,895 | 11/1957 | Peeps | 417/362 |
| 2,895,220 | 7/1959 | Johnston et al. | 433/92 |
| 3,078,579 | 2/1963 | Jones et al. | 433/92 |
| 3,138,873 | 6/1964 | Bishop | 433/92 |
| 3,308,609 | 3/1967 | McCulloch et al. | 55/429 |
| 3,429,313 | 2/1969 | Romanelli | 604/35 |
| 3,482,313 | 12/1969 | Stram | 433/92 |
| 3,780,502 | 12/1973 | Dupre et al. | 55/429 |
| 3,988,134 | 10/1976 | Gandrud | 433/92 |
| 4,133,658 | 1/1979 | Callewyn | 55/429 |

OTHER PUBLICATIONS

"Vacudent" brochure, Clinical Installations, Pre. 1980.
"Aeromedical Review, Central Dental Evacuation Systems", by Powell et al, May, 1982, USAF School of Aerospace Medicine.

*Primary Examiner*—John J. Wilson
*Attorney, Agent, or Firm*—Nixon & Vanderhye

[57] ABSTRACT

A dental vacuum assembly utilizes a rotary vane vacuum pump. The pump is operatively connected to a vacuum reservoir and driven by an electric motor commonly mounted with the pump on a vibration-isolated platform. The vacuum reservoir is operatively connected to a number of different dental stations, each including a dental aspirator tip. The vacuum reservoir is supported by a support component which receives a drain valve in the bottom of the vacuum reservoir, and has a false bottom connected to a drain pipe section which extends through a side wall of the support component for easy connection to a sewer.

18 Claims, 1 Drawing Sheet

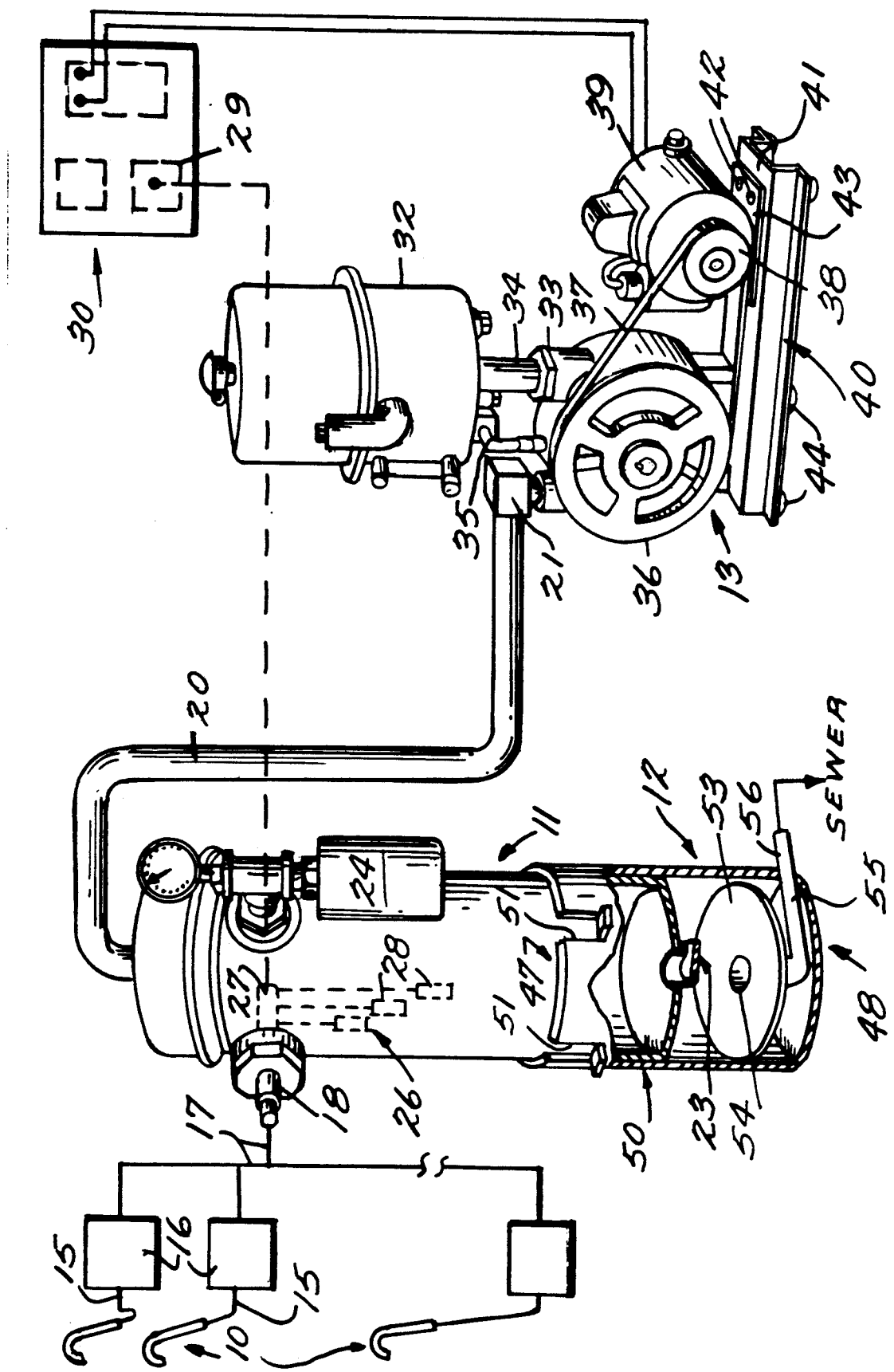

DENTAL VACUUM PUMP SYSTEM

This is a continuation of application Ser. No. 07/178,864, filed Apr. 4, 1988, now abandoned which in turn is a continuation of Ser. No. 477,519 filed Mar. 21, 1983, also abandoned.

BACKGROUND AND SUMMARY OF THE INVENTION

Modern dental care facilities usually include multiple operatories and a central vacuum system. Dental aspirator tips are provided at each operatory for disposition in the patient's mouth to remove aerosols, liquids, solid debris, and odors from the patient's mouth. Typical conventional dental vacuum systems have been far from ideal from the standpoints of noise output, vacuum intensity and flow rate charateristics, efficiency, and reliability. Typical commercially available dental vacuum systems include water ring or turbine vacuum pumps, and a back-up pump is normally specified because of the known unreliability of such pumps.

According to the present invention a dental vacuum system is provided that overcomes most of the drawbacks associated with conventional commercially marketed systems. The system according to the present invention has little noise, excellent efficiency, and ideal vacuum intensity and flow rate characteristics. The system also has excellent reliability and is easy to install and utilize in a central facility serving a number of dental operatories.

The system according to the invention includes a vacuum reservoir operatively connected to a rotary vane vacuum pump. The rotary vane vacuum pump, in the system combination, provides an effective vacuum intensity within a desirable range, irrespective of the practical number of operatories connected thereto. Additionally, the pump in the system of the invention may be operated by a small motor, such as a one horsepower electrical motor, yet it can effectively serve the same number of operatories served by a much larger power source in conventional dental vacuum facilities. The pump is preferably continuously lubricated utilizing an oil reservoir directly mounted thereon, and the pump and the motor are mounted on a common small platform in side-by-side relationship. A V-belt interconnects pulleys of the pump and motor to provide force transmission therebetween and elastomeric material feet are provided on the platform to facilitate desired noise control.

The vacuum reservoir, which is operatively connected to dental aspirator tips in a plurality of dental operatives, preferably comprises a cylindrical tank with a drain valve means, such as a rubber flap valve, disposed at the bottom thereof. A support and drain assembly provides for the ready connection of the vacuum reservoir to a drain. The support and drain assembly include a cylindrical support having a first end interior diameter slightly larger than the exterior diameter of the vacuum tank, with abutment portions of the tank and support and drain assembly operatively engaging to limit the penetration of the tank into the support and drain assembly. A false bottom is provided in the support and drain assembly immediately below the rubber flap valve, and a drain pipe extends from an opening formed in a center lowpoint of the false bottom through a side wall of the support and drain assembly, the drain pipe being readily connectable to the dental office's sewer system. The second end of the support and drain assembly supports the vacuum tank on a horizontal surface in a generally upright position.

It is the primary object of the present invention to provide an efficient and effective dental vacuum system. This and other objects of the invention will become clear from an inspection of the detailed description of the invention, and from the appended claims.

BRIEF DESCRIPTION OF THE DRAWING

FIG. 1 is a schematic view, partly in perspective and partly in block form, with portions of some components cut away for clarity of illustration, illustrating an exemplary dental vacuum assembly according to the present invention.

DETAILED DESCRIPTION OF THE DRAWING

The dental vacuum assembly illustrated in FIG. 1 includes as the major components thereof a plurality of dental aspirator tips 10, a vacuum reservoir 11 with support and drain assembly 12, and a rotary vane vacuum pump 13.

The dental aspirator tips 10 are conventional dental aspirator tips utilized in modern dental operatories. The tips 10 are put in the mouth of a reclining patient and remove aerosols, liquids, solid debris, and odors from the patient's mouth. An on-off valve (not shown) is commonly provided in each aspirator tip 10. Normally an aspirator tip 10 is provided in each dental operatory, with the vacuum reservoir 11, vacuum pump 13, etc. being provided at a central location. A flexible hose 15 connects each aspirator tip 10 to a conventional solids separator device 16, the devices 16 in turn being connected through vacuum conduit means 17 to the inlet 18 of vacuum reservoir 11.

The vacuum reservoir 11 preferably comprises a cylindrical vacuum tank, and is connected by a vacuum conduit 20 to the vacuum pump 13. Preferably a filter 21 is disposed in operative association with the conduit 20 (e.g. mounted directly on the pump 13 housing) to filter out any foreign material that may enter the line or conduit 20, so that it does not damage the rotary vane of the pump 13. The vacuum reservoir 11 stabilizes the vacuum intensity and stores material drawn through the vacuum plumbing, and —in combination with filter 21—prevents material drawn through the vacuum system from entering the pump 13. A commercially available vacuum reservoir 11 that may be utilized in the practice of the present invention is manufactured by Babson Bros. Co. of Oak Brook, Illinois, and sold under the trade name "Alamo". This reservoir includes a large foam filter, a baffled inlet 18, a rubber flap drain valve 23 provided at the bottom thereof, and would conventionally have a capacity of about 10 gallons. A conventional vacuum controller 24 is also associated therewith.

According to the present invention, disposed within the vacuum reservoir 11 is an improved liquid level sensor means, shown generally by reference numeral 26. The means 26 is sensitive to both foam and liquid, and preferably is in the form of a plurality of commercially available shielded electrodes 28 that are mounted in the reservoir 11—as by the support shown in dotted line at reference numeral 27—in a position so that the shielded electrodes 28 are remote from the splash area inside the reservoir 11. The automatic sensing means 26 are operatively connected to an appropriate liquid level sensing relay 29 in an electrical control panel 30 that may be located at any desirable position within the central area containing the reservoir 11, pump 13, etc.

The vacuum pump 13 according to the present invention comprises a low speed, positive displacement rotary vane vacuum pump, one that is preferably continuously lubricated by oil from an oil reservoir 32 mounted directly atop the pump housing by the air discharge outlet 33 and outlet pipe 34. Lubricating oil from the refillable reservoir 32 passes through oil line 35 and the like to lubricate the appropriate working parts of the pump 13. The rotary vane of the pump is driven by the relatively large diameter pulley 36, which is operatively connected by V-belt 37 to the relatively small diameter pulley 38 of a motor 39. The motor 39 preferably comprises an electrical motor (e.g. 1 h.p.) mounted in side-by-side relationship with the pump 13 on a common platform 40. Typical rotary vane vacuum pumps utilizable in the practice of the invention are illlustrated in U.S. Pat. Nos. 3,782,868; 4,164,384 and 4,276,005. One commercially available particularly desirable vacuum pump with continuous oiler is sold by Babson Bros. Co., of Oak Brook, Illinois, under the trademark 37 Alamo".

The platform 40 for mounting the pump 13 and motor 39 in side-by-side relationship comprises a simple platform structure having a generally flat horizontally extending top surface 41 in which are formed a plurality of vertically extending openings. Fasteners extend through the openings to connect the pump 13 and motor 39 to the surface 41. For instance screws 42 are illustrated in FIG. 1 connecting the base 43 of motor 39 to surface 41, and preferably screws (not shown) are threaded through openings formed in the surface 41 directly into interiorly threaded openings in the bottom of the pump 13 housing. In addition to providing easy installation, the platform 40 also minimizes noise. Elastomeric material (e.g. rubber) feet 44 are provided on the bottom of the platform 40 and provide the only interengagement between the platform 40 and a horizontal supporting surface.

In order to further facilitate easy installation of the assembly according to the present invention, the vacuum reservoir support and drain assembly 12 is provided. The structure 12 preferably comprises a cylindrical support component with a hollow interior, and having first and second ends 47, 48, respectively thereof. The first end 47 has an interior diameter slightly greater than the exterior diameter of the cylindrical reservoir tank 11. Radially extending flanges 50 may be provided extending from the exterior of the reservoir tank 11, and those cooperate with cut-outs 51 formed in the support component 12, the flanges 50 and cut-outs 51 providing abutment means for limiting the penetration of the reservoir tank 11 into the support component 12.

Disposed in the support component 12 between the ends 47, 48 thereof is a false bottom 53 having a central opening 54 formed at the low-point thereof, and preferably directly below the drain valve means 23. Operatively connected to the opening 54 is a drain pipe section 55 which passes through a side wall of the support component 12 to provide an end pipe connection 56 which may be readily connected to any conventional sewer structure at the location of the dental facility. The structure 12 stands up on the second end 48 thereof and supports the reservoir 11 with a vertical orientation.

The vacuum reservoir, pump, etc. according to the present invention are ideally suited for dental vacuum system use. The rotary vane displacement pump has ideal vacuum intensity and flow rate characteristics.

The system has good vacuum intensity at zero flow levels, but not too high as to be undesirable. The vacuum intensity is substantially constant as flow volume increases, up to the capacity of the pump, so that the vacuum intensity remains substantially the same whether one, two, or six dental operatories are connected up to the reservoir 11. Additionally the system has no water consumption and a minimal discharge to the sewer or septic system, and freedom from mineral deposits on moving pump surfaces. For a given electrical input the system according to the invention can provide up to three to four times the useful output of conventional dental vacuum systems utilizing a water ring or turbine vacuum pump, and can operate with greater reliability.

It will thus be seen that the assembly according to the present invention provides an efficient and effective dental vacuum source assembly. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and systems.

What is claimed is:

1. A high efficiency dental vacuum source assembly that utilizes substantially no water and provides a substantially constant source of vacuum intensity comprising:

a plurality of dental aspirator tips;
   a vacuum reservoir;
   a rotary van vacuum pump;
   a motor for powering said rotary vane vacuum;
   a vacuum line interconnecting said vacuum reservoir and said rotary vane vacuum pump; and
   vacuum conduit means connecting said plurality of dental aspirator tips to said vacuum reservoir.

2. An assembly as recited in claim 1 further comprising a filter disposed in said line connecting said vacuum reservoir and said rotary vane vacuum pump.

3. An assembly as recited in claim 1 further comprising oil reservoir means directly mounted to said rotary vane vacuum pump for continuously lubricating said pump.

4. An assembly as recited in claim 3 further comprising a platform; means for directly mounting said rotary vane vacuum pump and said motor in side-by-side relationship on said platform; and a drive means interconnecting said motor and said rotary vane vacuum pump for effecting driving of said pump by said motor when said pump and motor are in said side-by-side relationship.

5. An assembly as recited in claim 4 wherein said drive means comprises a V-belt, and a pair of pulleys, one pulley associated with said motor and the other pulley associated with said pump.

6. An assembly as recited in claim 5 wherein said motor is an electric motor.

7. An assembly as recited in claim 4 further comprising elastomeric material feet formed on the bottom of said platform, said feet providing the sole support of said platform on a horizontal supporting surface.

8. An assembly as recited in claim 3 wherein said vacuum reservoir includes a vacuum controller, and liquid level sensing means for sensing the volume of liquid or foam therein.

9. An assembly as recited in claim 8 wherein said vacuum reservoir includes drain valve means formed at the bottom thereof; and further comprising a support means for supporting said vacuum reservoir for facilitating operative connection of said drain valve means formed at the bottom thereof to a drain.

10. An assembly as recited in claim 8 further comprising solid separator means disposed between each dental aspirator tip in said vacuum reservoir and said conduit means interconnecting said aspirator tips and said vacuum reservoir.

11. An assembly as recited in claim 3 further comprising a filter disposed in said conduit connecting said vacuum reservoir and said rotary vane vacuum pump.

12. An assembly as recited in claim 1 further comprising a platform; means for directly mounting said rotary vane vacuum pump and said motor in side-by-side relationship on said platform; and a drive means connecting said motor to said rotary vane vacuum pump for effecting driving of said pump by said motor when said pump and motor are in said side-by-side relationship.

13. An assembly as recited in claim 12 further comprising elastomeric material feet formed on the bottom of said platform, said feet providing the sole support of said platform on a horizontal supporting surface.

14. An assembly as recited in claim 13 wherein said drive means comprises a V-belt, and a pair of pulleys, one pulley associated with said motor and the other pulley associated with said pump.

15. A dental vacuum assembly comprising:
a plurality of dental aspirator tips;
a vacuum reservoir;
a vacuum pump;
means for driving said vacuum pump;
a conduit interconnecting said vacuum reservoir and said vacuum pump;
conduit means interconnecting said plurality of dental aspirator tips and said vacuum reservoir;
drain valve means formed in the bottom of said vacuum reservoir; and
support means for said vacuum reservoir, said support means comprising: a hollow support component having first and second ends, said first end receiving said vacuum reservoir therein so that said drain valve means extends into the hollow interior of said support component; a false bottom formed in said support component between the first and second ends thereof; and a pipe section connected to an opening formed in said false bottom and extending therefrom through a side wall of said support component; said second end of said support component for engaging a support surface to support said vacuum reservoir in an upright position.

16. An assembly as recited in claim 15 wherein said vacuum reservoir comprises a cylindrical container; and wherein said support component comprises a cylindrical member having an internal diameter at said first end slightly greater than the external diameter of said vacuum tank; and further comprising a plurality of abutment means cooperating between said vacuum reservoir and said support component for limiting relative movement therebetween.

17. A dental vacuum source assembly comprising:
a plurality of dental aspirator tips;
a vacuum reservoir;
a rotary vane vacuum pump;
a motor for powering said rotary vane vacuum pump;
a vacuum line interconnecting said vacuum reservoir and said rotary vane vacuum pump;
vacuum conduit means connecting said plurality of dental aspirator tips to said vacuum reservoir;
drain valve means formed in the bottom of said vacuum reservoir; and
support means for said vacuum reservoir, said support means comprising: a hollow support component having first and second ends, said first end receiving said vacuum reservoir therein so that said drain valve means extends into the hollow interior of said support component; a false bottom formed in said support component between the first and second ends thereof; and a pipe section connected to an opening formed in said false bottom and extending therefrom through a side wall of said support component; said second end of said support component for engaging a support surface to support said vacuum reservoir in an upright position.

18. An assembly as recited in claim 17 wherein said vacuum reservoir drain valve means comprises a rubber flap valve means.

* * * * *